United States Patent [19]

Hanus

[11] Patent Number: 5,108,708
[45] Date of Patent: Apr. 28, 1992

[54] ALIQUOT COLLECTION ADAPTER FOR HPLC AUTOMATIC INJECTOR ENABLING SIMULTANEOUS SAMPLE ANALYSIS AND SAMPLE COLLECTION

[75] Inventor: James P. Hanus, Mesquite, Tex.

[73] Assignee: The United States of America as represented by the Secretary of the Department of Health and Human Services, Washington, D.C.

[21] Appl. No.: 210,005

[22] Filed: Jun. 22, 1988

[51] Int. Cl.⁵ .................. G01N 35/06; B01L 3/02
[52] U.S. Cl. .................. 422/100; 73/864.11; 73/864.25; 422/63
[58] Field of Search .............. 422/62, 63, 64, 65, 422/68.1, 99, 100, 103, 104; 436/43, 48, 51; 73/864.11, 864.25

[56] References Cited

U.S. PATENT DOCUMENTS

| | | | |
|---|---|---|---|
| 4,279,860 | 7/1981 | Smolen | 422/63 |
| 4,298,026 | 11/1981 | Ambers | 422/63 |
| 4,299,796 | 11/1981 | Hogen Esch | 422/63 |
| 4,318,885 | 3/1982 | Suzuki et al. | 422/68 |
| 4,424,191 | 1/1984 | Jakubowicz | 422/65 |
| 4,446,104 | 5/1984 | Hämmerling et al. | 422/63 |
| 4,495,149 | 1/1985 | Iwata et al. | 422/65 |
| 4,512,953 | 4/1985 | Marsoner et al. | 422/67 |
| 4,528,158 | 7/1985 | Gilles et al. | 422/63 |
| 4,649,028 | 3/1987 | Kaltenbach et al. | 422/100 |
| 4,830,832 | 5/1989 | Arpagaus et al. | 422/63 |

Primary Examiner—Jill A. Johnston
Attorney, Agent, or Firm—Lowe, Price, Leblanc & Becker

[57] ABSTRACT

A method and apparatus permitting automated tablet dissolution testing are provided. A multi-channel pump removes liquid dissolution media from a plurality of kettles and transfers this media to a plurality of vials held within the carousel of an autoinjector for HPLC analysis. Passages for returning dissolution media is provided between the supply pump or pumps and the vials. A mechanism is provided for cyclically switching the media flow from one mode, where the media flows from kettles to the vials, and another mode, where the media flows from the kettles to the return passages. Each vial in the apparatus may thus be simultaneously filled from a separate respective kettle at an appropriate time and the supply passages may be rinsed with the new dissolution media after a set of vials are filled with the previous dissolution media. The filled vials can be analyzed without manual transfer to an HPLC column. Cycling between filling and rinsing may be accomplished by a microprocessor.

6 Claims, 4 Drawing Sheets

ALIQUOT COLLECTION ADAPTER FOR HPLC AUTOMATIC INJECTOR ENABLING SIMULTANEOUS SAMPLE ANALYSIS AND SAMPLE COLLECTION

BACKGROUND OF THE INVENTION a. Field of the Invention

The present invention relates generally to automatable liquid sampling, and more particularly to automatable liquid sampling devices and methods for transferring aliquots of dissolved samples of pharmaceutical tablets from a kettle to an autoinjector of a high pressure liquid chromatograph (HPLC).

b. Background of the Invention

In tablet dissolution testing, a tablet is placed within a kettle having dissolution media therein. At various times during the dissolution process an aliquot of dissolution media from the kettle is removed and tested, usually by HPLC, to determine the extent to which the tablet has dissolved therein.

Automated tablet dissolution devices have previously been known in the art:

SASDRA TM, made by Technicon Instruments Corp has been marketed as an automated tablet dissolution device. The determinative step is ultraviolet absorption and depends strongly on fixed mixing channels to obtain a response that is on scale. To operate properly, a detergent must be added to all liquids flowing through the system. Generally sufficient volume is not available for the detector to reach "steady state" for a proper reading. In addition, delicate glass plumbing is required to interconnect the tubings. After reading, the aliquot is discarded and not available for confirmation by a second technique. Due to limited storage capacity the device is not well suited to analysis requiring more than 6 aliquots. In addition, the timer uses a plastic tape for programming which is very inconvenient and imprecise. The timer can only hold enough tape for about a 6 hour run. Only a single component may be determined.

A second device, made by Hansen Research, is similar to the one proposed in that the aliquots are deposited in an autoinjector carriage. However, in the Hansen Research design, the carriage must then be transferred manually to the autoinjector for determination. All aliquots must be collected before analysis may be performed. This unit is built about and dependent upon an effective autoinjector which, however, is not fully automatic since the operator must manually transfer the carriage to the injector after all aliquots have been collected. No provisions are made for depositing aliquots in sealed vials.

SUMMARY OF THE INVENTION

An object of the present invention is to overcome defects in the prior art, such as mentioned above.

A further object is to provide improvements in sampling.

Another object of the present invention is to provide a device for the automated analysis of tablet dissolution aliquots which overcomes the above-noted disadvantages of the prior art.

Yet another object of the present invention is to provide a device for the automated analysis of tablet dissolution aliquots which permits HPLC analysis without manual transfer of the aliquots to the autoinjector of an HPLC column.

Yet a further object of the present invention is to permit automated analysis of tablet dissolution samples from a plurality of tablet dissolution kettles.

One embodiment of the apparatus includes of a plurality (usually six, one for each dissolution kettle) "tees" (supply conduits) which are connected to at least two multi-channel (at least one channel per kettle) peristaltic pumps, one pump being for supply and one pump being for return. More pumps, preferably six, may be used. Of course, single channel supply and return pumps may be employed for each kettle, provided that their actions are properly coordinated in time. The third output of each tee is attached via suitable, e.g. Tygon TM, tubing to its own corresponding carefully positioned hole in the roof of the sample compartment of the autoinjector, the latter of which may be the same autoinjector used in the aforementioned Hansen device. A template facilitates the positioning and drilling of the holes in the injector without disassembly. As the appropriate collection time nears, the supply pump or pumps and return pump or pumps are started and the tubing purged with dissolution media from respective kettles. At the collection time, which is usually offset a short time to compensate for tubing volume, the return pump is stopped and the aliquots are deposited in the appropriate vials for collection. After the aliquot volume is collected the return pump is started, dissolution media in the tubing flows back to its respective kettles, and collection stops.

In another embodiment, a plurality of cannulas (supply conduits) are mounted within a guide block assembly. Each tube in the upper guide block is connected to a supply pump means, such as a supply pump or one channel of a multi-channel supply pump, and distributes the dissolution media from the kettles to respective cannulas fixed therein. The upper guide block is also mounted to a reciprocating means which in turn reciprocatingly moves the upper guide block with respect to a lower guide block provided therebelow. The cannulas extend into passages in the lower guide block. Each cannula has, at its lower portion, an outlet on the lateral periphery thereof, and an open, needle-shaped tapered end extending essentially normal to the outlet. Each passage of the lower guide block communicates with a respective channel communicating with a respective return line which returns dissolution media in the cannula of the respective kettle from which it was drawn. Below each channel is positioned a seal or plurality of seals within the passages for the cannulas.

In use, when the cannulas are in their lowermost position within the guide block assembly, the open needle-shaped tapered ends of the cannulas extend into the vials and liquid from the kettles flows into the upper guide block, and flows through respective cannulas. The peripheral outlets of the cannulas are each sealed within the lower guide block. Therefore, the dissolution media within each cannula flows into the vial associated with that cannula. At the appropriate time, the reciprocating means lifts the upper guide block and the cannulas held therein. The open ends of the cannulas retreat into the seals of the lower guide block, and the peripheral openings of the cannulas align with their return channels whereby dissolution media flows into the respective return lines and respective kettles so that the cannulas may then be rinsed with fresh dissolution media.

DETAILED DESCRIPTION OF THE PREFERRED EMBODIMENTS

Figure 1:
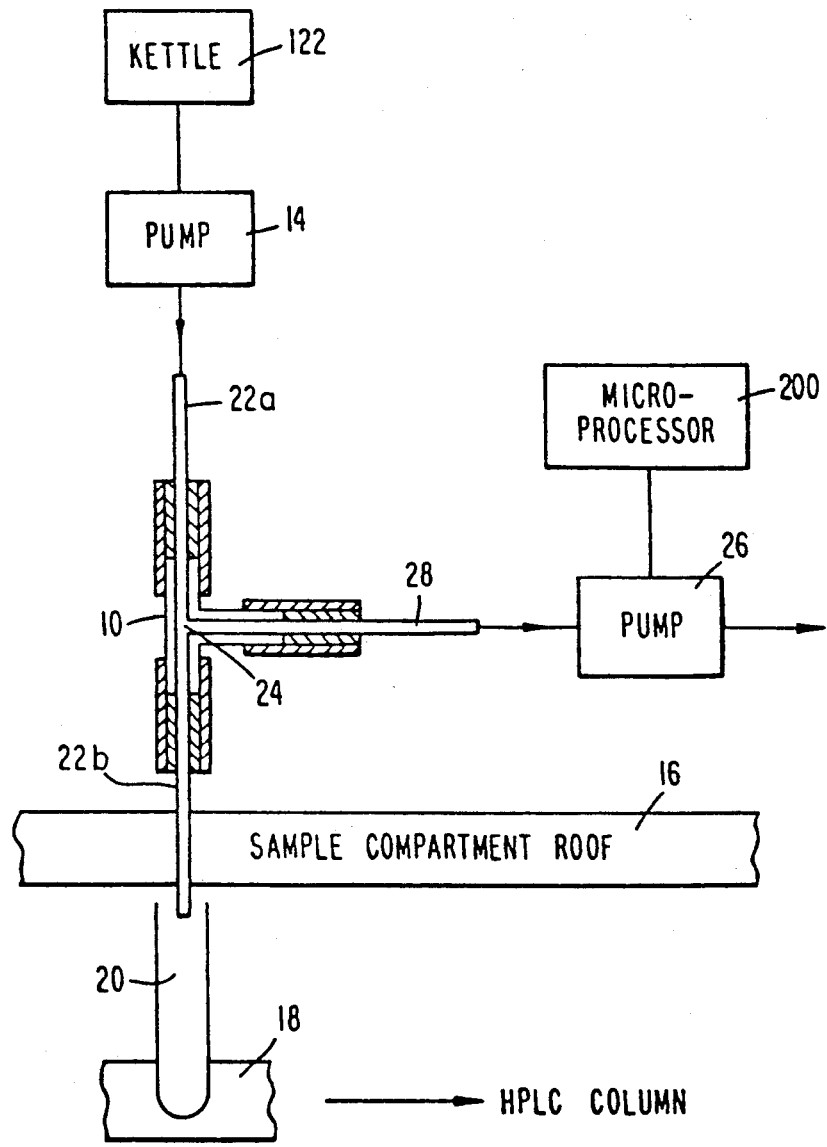
FIG. 1 shows a lateral cross-section of an embodiment of the present invention.
Figure 6:
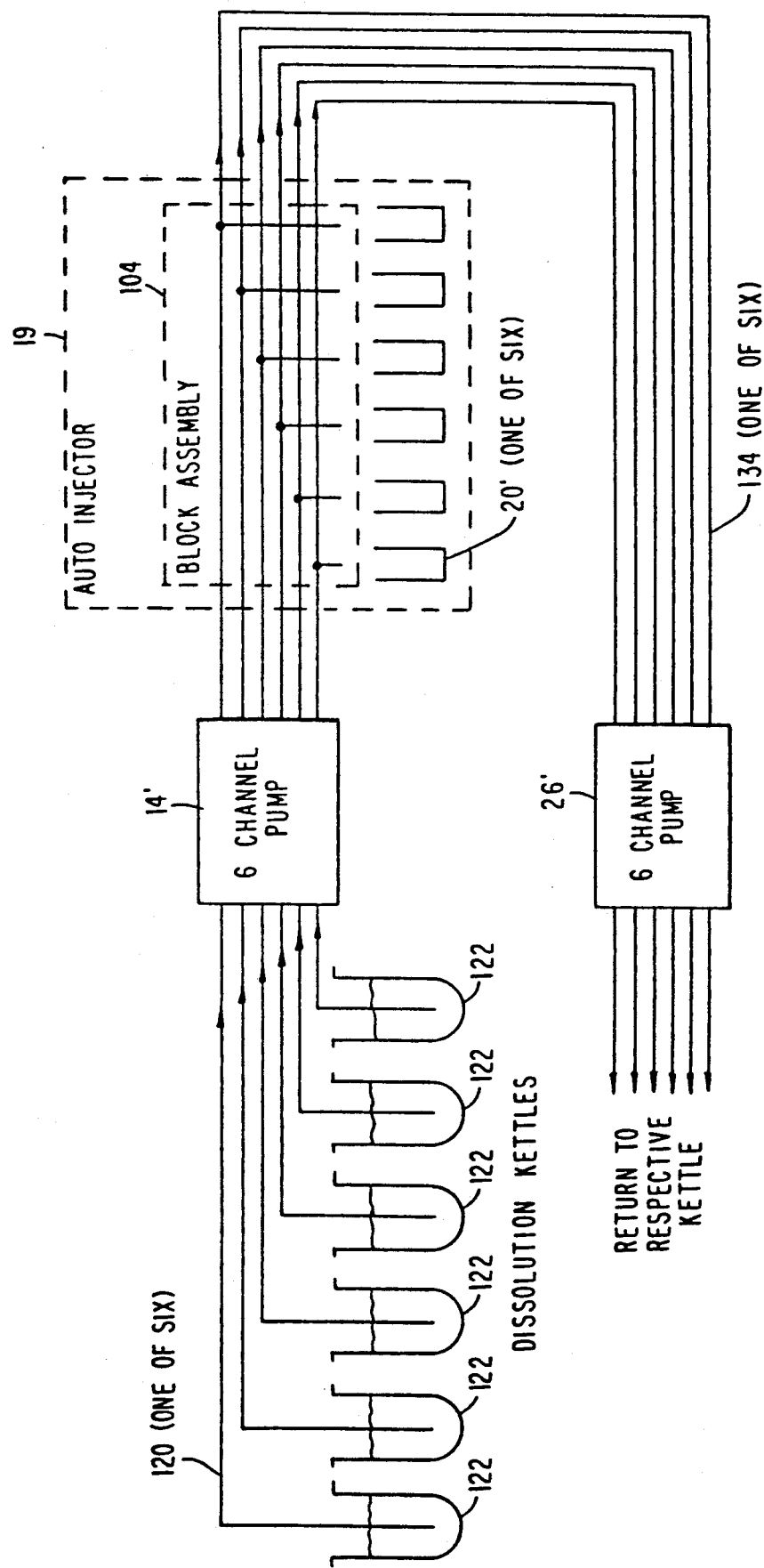
FIG. 6 is a schematic illustration showing the overall flow of dissolution media, exemplified using the embodiment shown in FIG. 2.

As shown in FIG. 1, each glass tee 10 is positioned within a set of Tygon TM sleeves slid over each branch thereof. The head of the tee defines a portion of a first passage extending from supply pump 14 for supplying a dissolution medium, through a sample compartment roof 16 in carousel 18 and into a sample vial 20 within the carousel 18 of HPLC auto-injector 19 (FIG. 6). A Teflon tube usually about 1/16 inch O.D., or a set of Teflon tubes 22 and 22b, extends through the head of the tee to complete the first passage. The first passage has opening 24 at the intersection between the tail of the tee. A return tube of Teflon extends from this opening, through the tail of the tee and the Tygon sleeve thereof, to a return pump 26 to define a return line 28. Generally the length of the portion of the first passage above opening 24 is large compared with the length of the portion of the first passage below the opening extending into the vial, in order to minimize the amount of media remaining below the opening after rinsing.

When dissolution media from a plurality (for, the sake of illustration, six) kettles is to be suppled to their respective sample vials for analysis, six-channel supply pump 14 is started while return pump 26 is shut off. After the dissolution media has flushed the fluid lines, return pump 26 is operated, typically at about twice the rate of supply pump 14, while dissolution media from the kettle rinses the tees. Each of the tees are connected to one respective channel of six-channel supply pump 14 and one respective channel of six-channel return pump 26. Thus a sample is simultaneously obtained from each of the six kettles, thus totalling six samples, one from each kettle.

Figure 2:
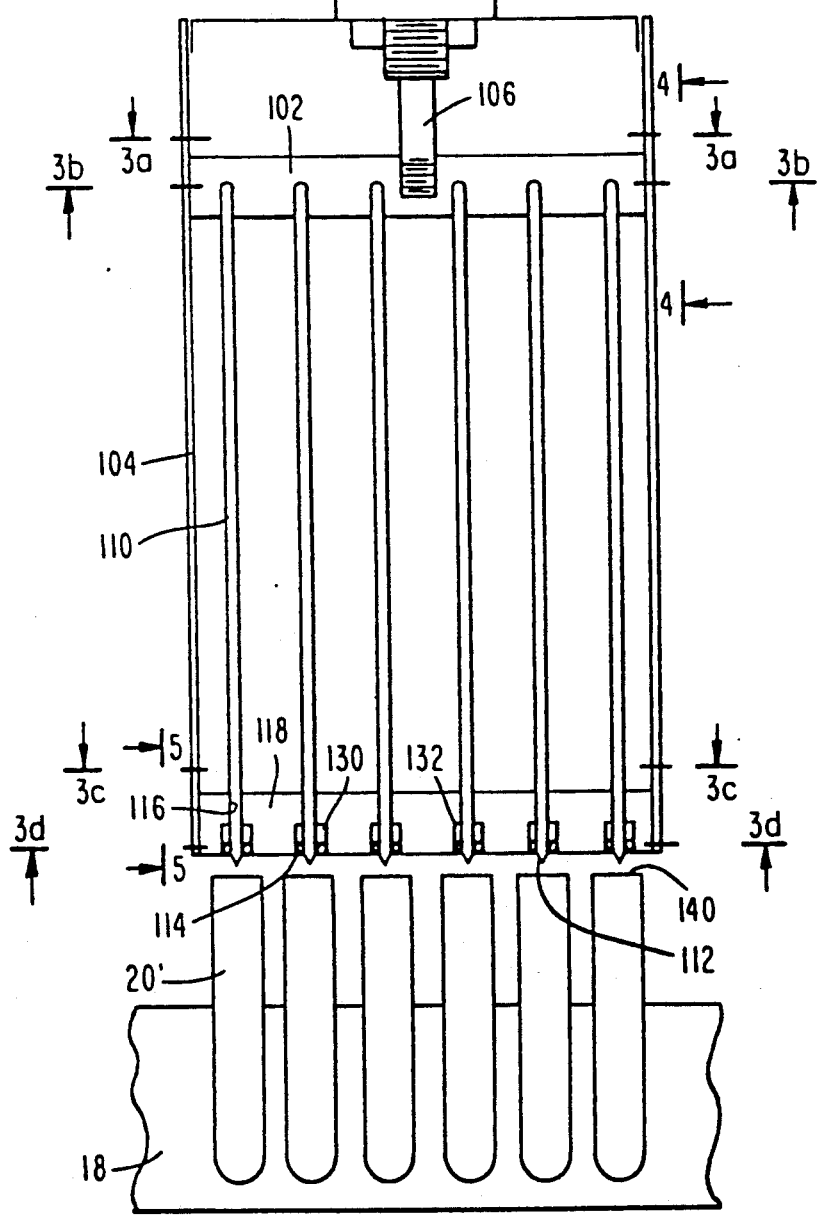
FIG. 2 is a schematic cross-section of another embodiment of the present invention.
Figure 3A:
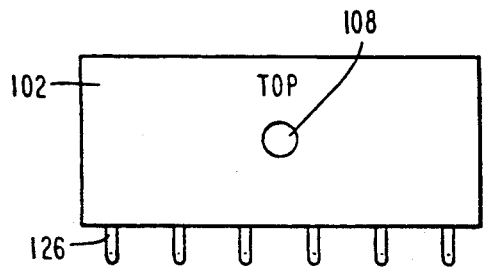
FIGS. 3a-3d are a series of cross sectional views taken along respective lines 3a-3d in FIG. 2, looking in the direction of the arrows.
Figure 3B:
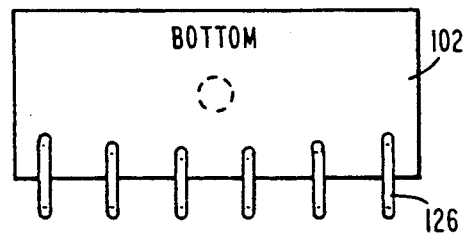
Figure 3C:
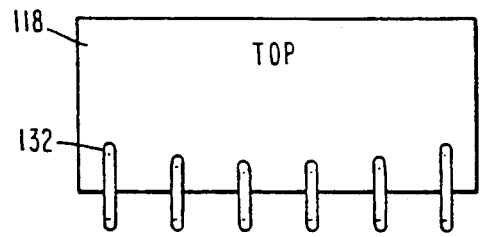
Figure 3D:
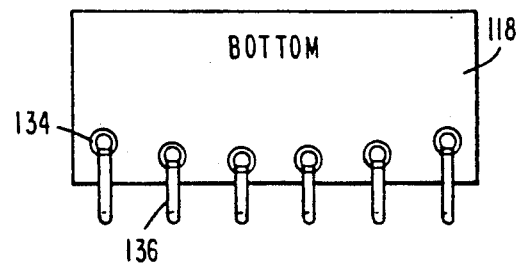
Figure 4:
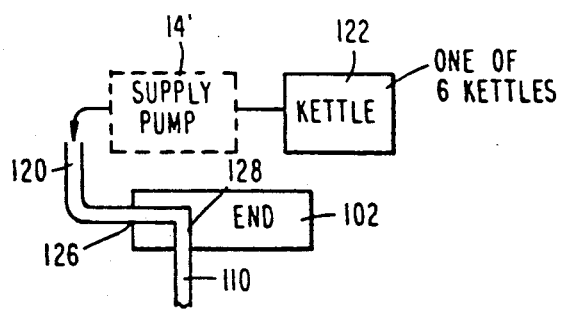
FIG. 4 is a cross-sectional view taken along line 4—4 in FIG. 2, looking in the direction of the arrows.
Figure 5:
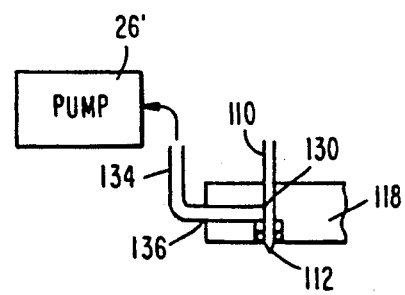
FIG. 5 is a cross-sectional view taken along line 5—5 in FIG. 2, looking in the direction of the arrows.

FIGS. 2 and 3a-3d show a second embodiment 100 of the present invention. As best shown in FIG. 2, upper guide block 102 of guide block assembly 104 is rigidly connected to a longitudinally reciprocating piston 106 of air cylinder 108. A plurality of needle-shaped cannulas 110 (one for each kettle), open, tapered distal ends 112, are rigidly fixed with upper guide block 102 and extend slidably through seals 114 at the bottom of passages 116 in lower guide block 118 of block assembly 104. Fluid then flows from each of six kettles 122, through respective cannulas 110, into their return lines 134.

As best shown in FIGS. 3a-3d, 4 and 5, a respective supply line 120 connects a channel of a supply pump means, such as pump 14', and dissolution media kettle 122 to tube connector inlets 126 extending rearward from upper guide block 102. Tube connector inlets 126 distribute the dissolution media from supply line 120 respective ones of the six cannulas 110 extending therethrough. Pump 14', which is optional, is shown in dot-dash form on FIGS. 4 and 6. If pump 14' is eliminated, return pump 26' also serves to pump, by suction, dissolution media through supply line 120.

The lower ends of cannulas 110 have openings 130 on the peripheries thereof. When ends 112 of cannulas 110 are retracted (i.e., when piston 108 is retracted), openings 130 align with channel or channels 132 in guide block 118. Respective channels 132 then connects each opening 130 of cannulas 110, with its respective return line 134, to return pump 26' via lower guide block 118.

When piston 106 is extended, at the appropriate time, openings 130 are blocked by seals 114 in passages 136. Thus, fluid flows from kettle 122, past blocked openings 130, and into vials 20'.

Presently, this invention is used with independent generic microcomputer 200 (FIG. 1) or 200' (FIG. 2) to synchronize the aliquot collection. In this configuration, the computer and injector are running two different programs which are only synchronized by a single start signal. After the start, the two programs must remain synchronized so that the injector is in the proper position for collecting the successive aliquots. This limits the HPLC analysis time to a maximum of 8 minutes. If a longer analysis time is required the aliquots must be collected first and then analyzed after the entire collection program has been completed. So far all tablets tested have been capable of being analyzed in less than 8 minutes. For longer analysis times the autoinjector will have to be controlled asynchronously. An interface box is presently being developed which will enable the autoinjector to be aschronously controlled by about any general purpose inexpensive microcomputer. Asynchronous control will enable longer analysis times to be used and in addition will enable unrelated but similar samples to be analyzed as priority samples without having to wait for the dissolution to be completed. Using the microcomputer and asynchronous control any number of aliquots may be collected over any time period up to several days. The operator only needs to check the injector about every 12 hrs and back-fill the full vials with empty vials.

The design of the FIGS. 2-5 embodiment has several useful features. It is a flow through design and is completely washed with the fresh aliquot each collection cycle. With the seals in the guide block, one of the pump mechanisms may be eliminated. When the cannula are down, the inlets to the return pump are partially blocked and not aligned with the liquid path. In this case the six return pump channels may be located on the same pump as the supply channels. Moving the cannula down has the same effect as turning off an individual pump. This feature alone can save about $800, the price of the bare pump drive mechanism. This device is mounted directly against the upper surface of the sample compartment roof and aligned with holes in roof. It is capable of piercing self-sealing silicone rubber septa 140 to deposit aliquots in sealed vials. It can deliver as little as 100 microliters to the bottom of limited volume inserts to eliminate trapped bubbles in tip of these inserts.

In the embodiment of FIGS. 2-5, the typical dimensions are as follows:

height of entire guide block assembly: 5 in. distance between upper and lower guide blocks: 4 in. height of upper and lower guide blocks: ½ in. each length of upper and lower guide blocks: 2 in. each width of upper and lower guide blocks: ⅜ in. each outer diameter of cannulas: each 1/16 in. stainless steel.

Of course, to avoid unwanted retention of dissolution media in the cannulas, the peripheral holes should be provided as close to the ends of the needle shaped cannula tips as possible.

In each design a single supply line and pump may supply fluid from one kettle to several cannulas. Also, one pump may pump dissolution media from several kettles into distinct vials via the cannulas. In the second embodiment of the invention, the upper guide block and/or the lower guide block would, in those circumstances, be designed to accommodate multiple distinct flows of dissolution media by providing the appropriate arrangement of distribution return channels for each pair of cannulas.

While specific embodiments of the present invention have been disclosed in the foregoing description, it will be understood that various modifications within the scope of the invention may occur to those skilled in the art. For example, each kettle may be connected to more than one vial. Therefore it is intended that adaptations and modifications should and are intended to be comprehended within the meaning and range of equivalents of the disclosed embodiment.

What is claimed is:

1. In combination, a plurality of kettles and a device for transferring dissolution media from a plurality of kettles to a plurality of vessels, comprising:

a plurality of kettles containing respective dissolution media;

supply pump means for removing said dissolution media from said kettles, said supply pump means having a separate supply channel for each of said kettles;

respective separate supply conduits for receiving dissolution media pumped from said separate supply channels;

a plurality of vials in fluid communication with respective separate supply channels via said separate supply conduits;

a carousel for holding said plurality of vials therein; and switchable fluid return means comprising switching control means for switching between operative and nonoperative modes and having a separate fluid return passage positioned between each said supply channel and each said vial, for removing fluid, pumped by said supply pump means into said supply conduits, which, when operative, causes said dissolution media to flow from said kettles, through said supply conduits, and into said respective fluid return passages so that essentially no dissolution media flows into said plurality of vials, wherein, when said return means is inoperative, dissolution media flow from said kettles through said supply conduits and into corresponding vials, bypassing said return passages, a guide block assembly is positioned between said supply pump means and said plurality of vials, said guide block assembly comprising an upper guide block rigidly mounted to longitudinally reciprocating means, each of said supply conduits comprising a cannula rigidly mounted to a bottom portion of said upper guide block, said cannula having a tapered, needle-shaped lower end and an opening in the periphery thereof, said upper guide block having a plurality of separate inlets each in fluid communication with a respective supply channel, said inlets distributing dissolution media received therein to respective cannulas, a lower guide block through which the lower end of each cannula extends, each cannula extending through a respective longitudinal passage in said lower guide block, and each longitudinal passage having a peripheral seal which is aligned with and seals said peripheral opening in the cannula extending therethrough when said reciprocating means is extended downward, and each longitudinal passage having a respective return channel above said seal, said return channel aligning with said peripheral opening of said cannula when said reciprocating means is retracted upward, whereby dissolution media are pumped from said kettles into said inlets, through said cannulas and into said vials when said reciprocating means is downwardly extended, and dissolution media flow from said kettles through said inlets and said cannulas and into said return passages when said reciprocating means is upwardly retracted.

2. The combination of claim 1, wherein said reciprocating means is pneumatic cylinder having its piston fixed to said upper guide block.

3. The combination of claim 1, wherein said cannulas are made of stainless steel.

4. The combination of claim 1, wherein a top end of each said vial is sealed by self-sealing septa, the septa being punctured by said tapered ends of said cannulas when said reciprocating means extends downwardly, and resealing when said reciprocating means is upwardly retracted.

5. The combination of claim 1, wherein said return means also functions as said supply pump means.

6. The combination of claim 1, wherein said plurality of vials comprises six vials.

* * * * *